United States Patent [19]

Brunell

[11] Patent Number: 5,056,508
[45] Date of Patent: Oct. 15, 1991

[54] NECK SUPPORT FOR CERVICAL OR WHIPLASH PROBLEMS

[76] Inventor: Gladys B. Brunell, 237 Park Ave., Worcester, Mass. 01609

[21] Appl. No.: 594,431

[22] Filed: Oct. 9, 1990

[51] Int. Cl.$^5$ .......................... A61H 1/02; A61F 5/04
[52] U.S. Cl. ................................... 128/75; 128/87 B; 128/DIG. 23
[58] Field of Search ............... 128/87 B, 75, DIG. 23, 128/94, 875, 876, 874, 76 L

[56] References Cited

U.S. PATENT DOCUMENTS

| | | | |
|---|---|---|---|
| 1,510,187 | 9/1924 | Martin | 128/DIG. 23 |
| 1,964,962 | 7/1934 | Rosenblum | 128/87 B |
| 1,991,677 | 2/1935 | Jacks | 128/94 |
| 2,874,468 | 2/1959 | De Woskin | 128/75 |
| 3,706,310 | 12/1972 | Garnett | 128/94 |
| 3,850,164 | 11/1974 | Hare | 128/DIG. 23 |
| 4,204,529 | 5/1980 | Cochrane | 128/75 |
| 4,327,909 | 5/1982 | Neufeld | 128/94 |
| 4,437,459 | 3/1984 | Slavetskas | 128/94 |
| 4,576,150 | 3/1986 | Auracher | 128/75 |
| 4,641,642 | 2/1987 | Williams, Jr. | 128/875 |

*Primary Examiner*—Robert A. Hafer
*Assistant Examiner*—Michael Brown
*Attorney, Agent, or Firm*—Charles R. Foy

[57] ABSTRACT

A back of the neck support collar including an elongated, flexible member having a stiffened central portion to apply to the nape, and extending end portions for tying or temporary attachment to the user or to a body harness, to maintain the stiffened portion in firm position to hold the neck immobile or nearly so. The flexible member is provided with stretch areas, and can be used in pairs for greater flexibility as to the areas to be treated.

4 Claims, 2 Drawing Sheets

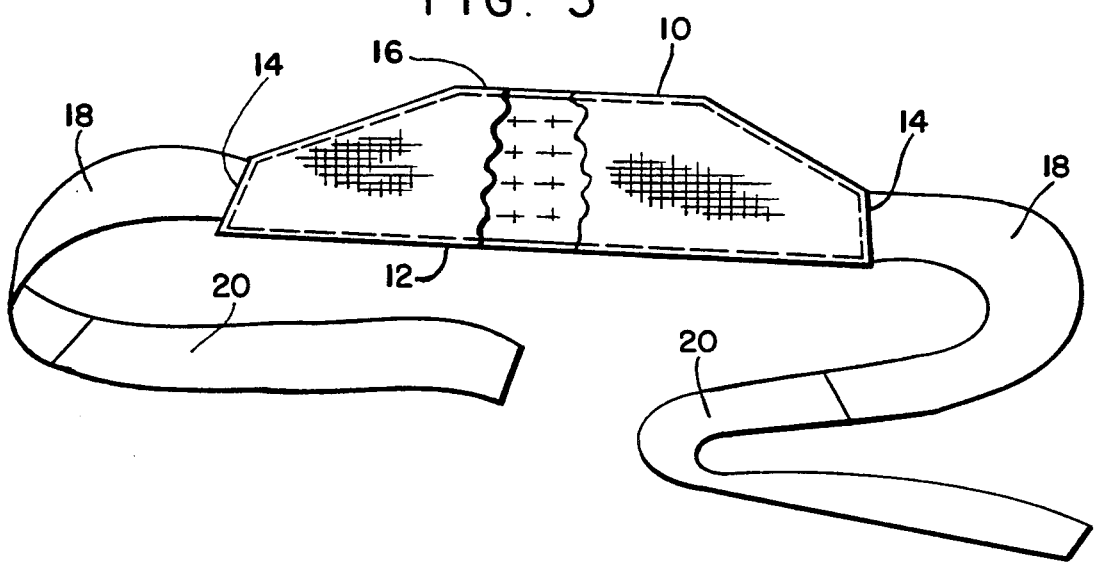
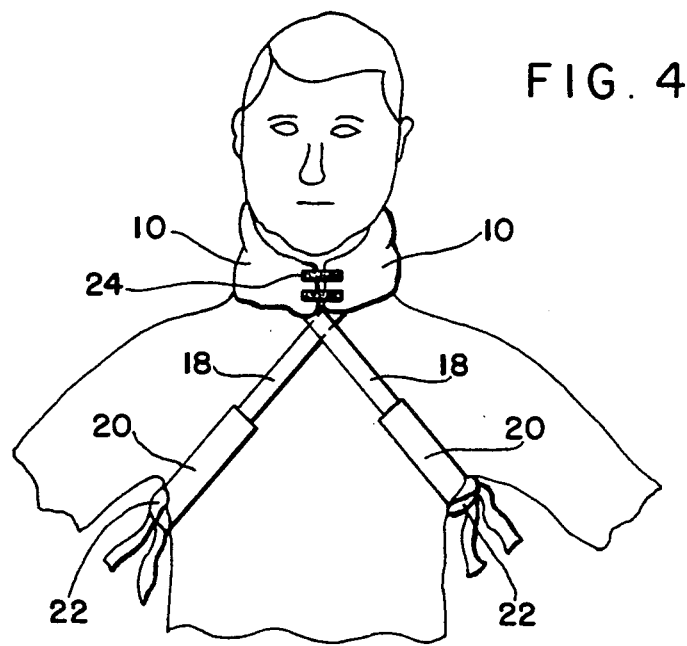

NECK SUPPORT FOR CERVICAL OR WHIPLASH PROBLEMS

BACKGROUND OF THE INVENTION

There are several cervical collars for the amelioration of such problems but they are heavy, clumsy, or in general not for women and especially not for frail persons and those with tender features. Those collars that are presently available are obvious, unpreposing and certainly do nothing to add to the looks of a person's attire. This invention is easy to apply to the body in different appearances, positions, and varied situations. One condition that is greatly helped with a minimum of obtrusiveness is spondylosis, but whiplash is also treatable with the present neck support.

SUMMARY OF THE DISCLOSURE

One of the inventive concepts in this invention resides in the fact that it is of frameless fabric, flexible and light weight, and can be used to advantage in multiples. Each unit is like any other unit, but can be rearranged to fit the person, if this seems to be advantageous. These units may be separate, as one at each side of the neck, or they may overlap and assist each other.

Light weight, smooth and strong materials are used and there are no sharp edges or corners to be encountered. Basically, the Brook's Neck support is like a neck-tie in weight and some fabrics and consists of a central neck engaging member that may include an envelope or the like of soft, light fabric with a stiffener inside of any convenient type, i.e., foam, fiber fill, padding, quilted material, etc. To the ends of this central member there are elastic tapes, and to these are added cotton tying tapes. Thus, the center support is placed where needed at any position about the neck, the ends are brought under the arms under elastic pressure, and the tapes are used to firmly tie the support in the positions needed, whether used singly or in multiples.

BRIEF DESCRIPTION OF THE DRAWINGS

FIG. 3 is a view of a Brook's body support; and

FIG. 4 is a front view of a possible variation for whiplash.

PREFERRED EMBODIMENT OF THE INVENTION

The body support of this invention is best seen in detail in FIG. 3 wherein it is indicated at 10 and is essentially a two inch high fabric envelope about 8 inches along its base line 12, one inch at the ends 14, and four inches along the top edge 16. It is conveniently made of any fabric such as cotton, silk, polyester, etc., and contains a like proportioned stiffening material, e.g. foam rubber, fiber fill, quilting, etc. The complete envelope is narrow, e.g. one quarter of an inch, and several envelopes can be stacked or overlapped to add to the strength of the whole, where needed. All of the materials should not be of any kind of skin irritationer and colors will be the kind ordinarily found in garments to blend in. Attached to the envelope at the ends 14 are stretch tapes 18 of convenient length, e.g. six inches or so, and these terminate in non-stretch tie-tapes 20, as long as desired, about 14 to 18 inches.

Figure 1:
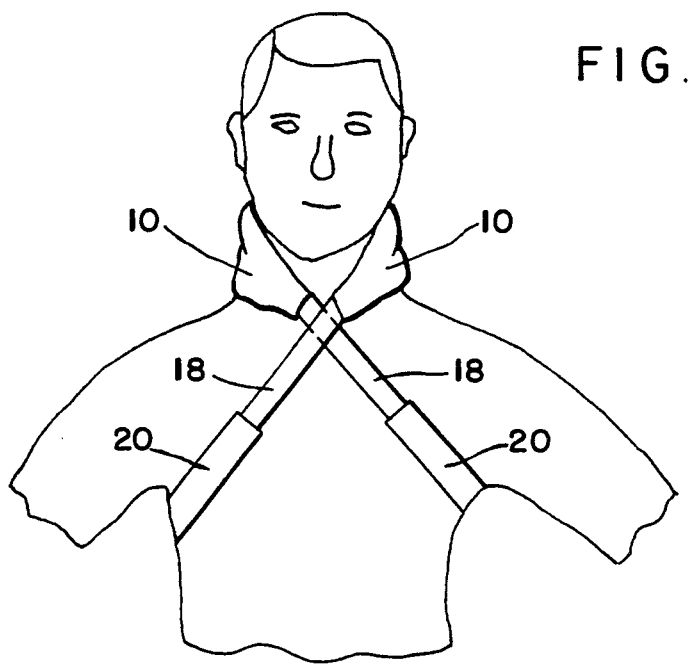
FIG. 1 is a front elevational view of a person using two of the new body supports, one at each side of the neck.
Figure 2:
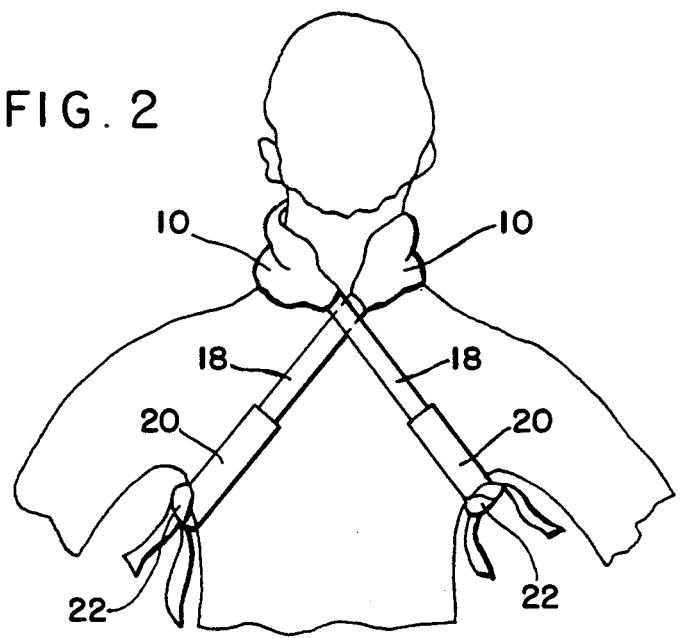
FIG. 2 is a rear view thereof.

The base or envelope 10 is applied to the area of need, at the nape or at the side area of the neck and the ties are passed under the arms and tied as desired. FIG. 1 shows two supports, one at each side of the neck of the user, and these can be placed so as to be separate or overlapped and then tied under the arms as at 22.

The above applies especially to spondylosis and cervical injuries but the same construction basically is usable for whiplash, the parts being larger and stronger and joined at the neck by catch and hold fastener material like "Velcro", as shown at 24 in FIG. 4. The ties, etc., would be the same, but the Velcro neck prevents the patient from bending his neck, while the spondylosis type leaves the throat open.

Both models may be made in small, medium, and large, and of the same or similar materials.

I claim:

1. A support for the nape and sides of the neck of a patient comprising:

an elongated fabric envelope having a central portion and opposite ends portions, said central portion being of a generally uniform height, each of said end portions being tapered from the height of said central portion to an end of substantially reduced height, the length of said envelope being sufficient to extend over the nape and partially around the sides of the neck without fully encompassing the neck.

strengthening material in the envelope;

a pair of stretch tapes each with opposite ends, one of said stretch tapes being secured at one of its ends to one end of said envelope, with the other stretch tape being secured at one of its ends to the other end of said envelope, and non-stretch ties secured to the other ends of the stretch tapes, said envelope being narrow throughout its length and constructed to suitably fit the nape of the neck or the sides of the neck of a patient;

and said tapes being of lengths to accomodate themselves to passing under the arms of the patient and being tied together under conditions of variable tightness due to the stretch tapes.

2. The support of claim 1 wherein the envelope is substantially flat.

3. The support of claim 2 wherein the envelope of one support can be stacked on the envelope of another support and used in multiple.

4. The support of claim 2 wherein the envelope of one support can be overlapped relative to the envelope of another support and used in multiples.

* * * * *